United States Patent
Koenig et al.

(10) Patent No.: US 6,289,236 B1
(45) Date of Patent: Sep. 11, 2001

(54) METHODS AND APPARATUS FOR DISTINGUISHING INFLAMED AND TUMOROUS BLADDER TISSUE

(75) Inventors: Frank Koenig, Berlin (DE); Francis J. McGovern, Lexington, MA (US); Thomas F. Deutsch, Cambridge, MA (US); Kevin T. Schomacker, Maynard, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/169,202

(22) Filed: Oct. 9, 1998

Related U.S. Application Data (60) Provisional application No. 60/062,026, filed on Oct. 10, 1997.

(51) Int. Cl.[7] .................................................. A61B 5/00
(52) U.S. Cl. ............................................................ 600/477
(58) Field of Search ..................................... 600/473, 475, 600/476, 477, 478; 356/318

(56) References Cited

U.S. PATENT DOCUMENTS

| | | | |
|---|---|---|---|
| 5,590,660 | * 1/1997 | MacAulay et al. | 128/664 |
| 5,647,368 | * 7/1997 | Zeng et al. | 128/665 |
| 5,769,792 | * 6/1998 | Palcic et al. | 600/477 |

OTHER PUBLICATIONS

Svanberg et al.,"Laser Spectroscopy in Tissue Characterisation", *Biomedical Optical Spectroscopy and Diagnostics*, 172–174, Mar. 20–22, 1996, Orlando, Florida.

Anidjar et al., "Laser Induced Autofluorescence Diagnosis of Bladder Tumors: Dependence on the Excitation Wavelength," *The Journal of Urology*, 156:1590–1596, Nov. 1996.

Baert et al., "Clinical Fluorescence Diagnosis of Human Bladder Carcinoma Following Low–Dose Photofrin Injection," *Urology*, 41:322–330, Apr. 1993.

D'Hallewin et al., "Fluorescence Imaging of Bladder Cancer," *Acta Urologica Belgica*, 62:49–52, 1994.

Koenig et al., "Laser Induced Autofluorescence Diagnosis of Bladder Cancer," *The Journal of Urology*, 156:1597–1601, Nov. 1996.

Koenig et al., "Spectroscopic Measurement of Diffuse Reflectance for Enhanced Detection of Bladder Carcinoma" *Urology*, 51:342–345, 1998.

Lam et al., "Detection of Dysplasia and Carcinoma in situ with a Lung Imaging Fluorescence Endoscope Device," *The Journal of Thoracic and Cardiovascular Surger*, 105:1035–1040, Jun. 1993.

Lin et al., "Native Fluorescence of Basal Cell Carcinoma is Predictive of Epidermal Proliferative Activity," *The Journal of Investigative Dermatology*, 104:634A, Apr. 1995.

Mourant et al., "Spectroscopic Diagnosis of Bladder Cancer with Elastic Light Scattering," *Lasers in Surgery and Medicine* 17:350–357, 1995.

Wang et al., "Fluorescence Endoscopic Imaging of Human Clonic Adenomas," *Gastroenterology*, 111:1182–1191, Oct. 1996.

* cited by examiner

*Primary Examiner*—Marvin M. Lateef
*Assistant Examiner*—Eleni Mantis Mercader
(74) *Attorney, Agent, or Firm*—Fish & Richardson P.C.

(57) ABSTRACT

The invention features an apparatus and methods for distinguishing inflamed tissue from cancerous tissue using autofluorescence.

17 Claims, 7 Drawing Sheets

FIG. 7

METHODS AND APPARATUS FOR DISTINGUISHING INFLAMED AND TUMOROUS BLADDER TISSUE

CROSS REFERENCE TO RELATED APPLICATION

This application claims priority from U.S. Provisional Application Serial No. 60/062,026, filed Oct. 10, 1997, which is incorporated herein in its entirety.

STATEMENT AS TO FEDERALLY SPONSORED RESEARCH

Funding for the work described herein was provided by the federal government, which may have certain rights in the invention.

BACKGROUND OF THE INVENTION

This invention relates to distinguishing inflamed bladder tissue from cancerous bladder tissue.

Transitional cell carcinoma (TCC) of the bladder is one of the more common cancers of both men and women in the United States. In 1995, for example, approximately 50,000 new cases were diagnosed, and about 11,000 individuals died of the disease.

In approximately 50 to 65% of cases, TCC lesions are superficial at presentation; however, despite apparently adequate transurethral resection of the tumor, the recurrence rate is about 55 to 70%. Since early malignant and dysplastic lesions are often invisible or barely visible, random biopsies are often recommended in addition to resection of the visible tumor to more accurately diagnose and/or stage the bladder tumor.

Diagnosis and staging of early stage bladder dysplasia can be complicated by the presence of inflamed tissue in the bladder. The similar appearance of inflamed tissue and the early stages of bladder cancer, such as carcinoma in situ, can make it difficult to distinguish between these lesions and cancerous cells. Thus, early malignant and dysplastic lesions can be overlooked because their appearance is similar to that of inflamed tissue.

SUMMARY OF THE INVENTION

The invention is based on the discovery that healthy bladder tissue, inflamed bladder tissue, and cancerous bladder tissue, each have distinct autofluorescence emission profiles centered at about 385 and 455 nm when illuminated with radiation centered at about 337 nm. Accordingly, the invention features methods and an apparatus for detecting cancerous tissue and distinguishing inflamed and cancerous tissue.

In general, the invention features methods for distinguishing cancerous tissue from inflamed tissue in a patient by (a) exposing a target tissue suspected of containing inflamed or cancerous tissue to incident radiation; (b) detecting autofluorescence emitted at a first and second wavelength upon irradiation of the target tissue with the incident radiation; and (c) comparing the autofluorescence emitted at the first wavelength with the autofluorescence emitted at the second wavelength. A decrease in autofluorescence at the first wavelength compared to autofluorescence emitted at the second wavelength indicates cancerous cells within the target tissue.

The incident radiation can have a wavelength between, e.g., 325 and 350 nm, 330 nm and 343 nm, 335 and 340 nm, or can be 337 nm. The emitted autofluorescence at the first wavelength can be between, e.g., 370 and 400 nm, 377 and 393 nm, or can be about 385 nm. The emitted fluorescence at the second wavelength can be between e.g., 440 and 470 nm, 450 and 460 nm, or can be centered at about 455 nm.

The patient can be, e.g., a human, a non-human primate, dog, cat, cow, or horse. The tissue can be an epithelial tissue, e.g., bladder, colon, cervix, esophagus, or lung.

The method can be performed in the presence of a sensitizing agent, or without a sensitizing agent.

In some embodiments, the incident radiation is one that causes collagen and reduced nicotine adenine dinucleotide phosphate (NADPH) or reduced nicotine adenine dinucleotide (NADH) to autofluoresce. The radiation emitted at the first wavelength can be a wavelength where the autofluoresence is dominated by collagen autofluoresence, and the radiation emitted at the second wavelength is a wavelength which is dominated by NADPH or NADH autofluoresence.

In another aspect, the invention provides an apparatus for distinguishing cancerous and inflamed tissue, where the apparatus has (a) a light source; (b) a first detector to detect autofluoresence emitted from the irradiated target tissue at a first wavelength; (c) a second detector to detect autofluoresence emitted from the irradiated target tissue at a second wavelength; and (d) an analyzer that compares a threshold value to the ratio of the autofluoresence at the first wavelength and the autofluoresence at the second wavelength. A ratio below the threshold value indicates that the analyzed tissue is cancerous, and a ratio above the threshold indicates that the analyzed tissue is inflamed. The threshold value can be adjusted to, e.g., 0.9, 1, 1.01, 1.1, 1.3, or 1.78, depending on the desired degree of specificity and sensitivity. A low threshold value will result in fewer tissues being scored as cancerous, while a high threshold value will result in more samples being scored as noncancerous.

In yet another aspect, the invention provides a method for distinguishing cancerous tissue from inflamed tissue in a patient by (a) exposing a target tissue suspected of containing inflamed or cancerous tissue to incident radiation; (b) detecting autofluoresence emitted at a first and second wavelength upon irradiation of the target tissue with the incident radiation; and (c) comparing a threshold value to a ratio of the autofluoresence at the first wavelength and the autofluoresence at the second wavelength. A ratio below the threshold value indicates that the analyzed tissue is cancerous, and a ratio above the threshold indicates that the analyzed tissue is inflamed.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention offers important advantages. First, cancerous lesions can be detected and distinguished from inflammatory lesions in vivo with the advantage that the number of biopsies from non-malignant tissues can be decreased or eliminated. In addition, the method does not require the use of systemic or topically applied sensitizing agents.

Other features and advantages of the invention will be apparent from the following detailed description, and from the claims.

DETAILED DESCRIPTION

Inflammatory lesions, e.g., of the human bladder, can be difficult to distinguish from cancerous tissue, e.g., flat and micropapillary malignancies. The present invention provides an apparatus and method for using laser induced autofluorescence to distinguish these tissue types. This is accomplished by irradiating a target tissue, e.g., a bladder tissue, with radiation that induces the target tissue to autofluoresce. By measuring the intensity of the autofluorescence at two wavelengths and then determining the ratios of the autofluoresence intensities at these wavelengths, it is possible to distinguish inflamed tissue from cancerous tissue.

Figure 1:
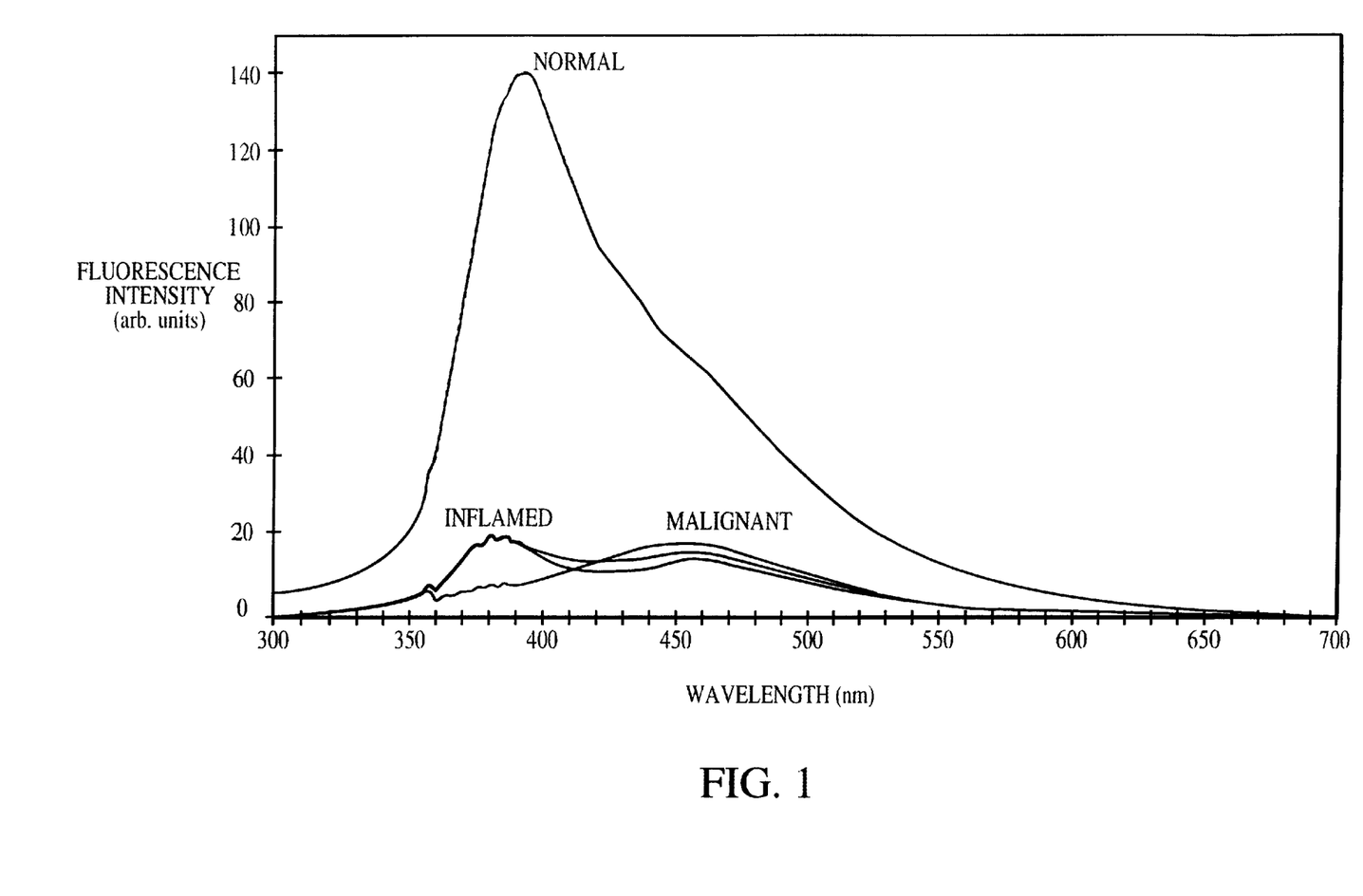
FIG. 1 is a series of typical autofluoresence spectra of normal, inflamed, and malignant human bladder tissue.

For example, when bladder tissue is excited at 337 nm, two autofluoresence emission maxima centered at 385 nm and 455 nm are observed (FIG. 1). The first maximum corresponds to the emission spectra of pure collagen (emission peak at approximately 385 nm). The second maximum corresponds to peaks associated with NADPH (emission peak at approximately 455 nm) and reduced nicotine adenine dinucleotide (NADH) (emission peak at approximately 465 nm). As can be seen in FIG. 1, the autofluorescence of normal urothelium is up to 20 times greater than the peak of cancerous and inflamed lesions of the human bladder. Emission spectra corresponding to cancerous tissue and inflamed lesions can also be distinguished from each other. While inflammatory tissue has two autofluoresence maxima at 385 and 455 nm, the typical spectra of cancerous lesions generally show maxima only at 455 nm. Thus, inflamed tissue can be distinguished from cancerous tissue based on their respective autofluorescence at 385 nm and 455 nm. In particular, the ratio of autofluoresence intensities at 385 and 455 nm (I385:I455) can be used to distinguish between inflamed tissue and cancerous bladder lesions. It has been empirically determined that a ratio greater than 1.01 is indicative of an inflamed but noncancerous lesion, while a ratio of less than 1.01, is indicative of a cancerous lesion.

The present invention provides an apparatus and methods for distinguishing inflamed and cancerous bladder tissue.

Apparatus for Detecting Autofluorescence

Figure 2:
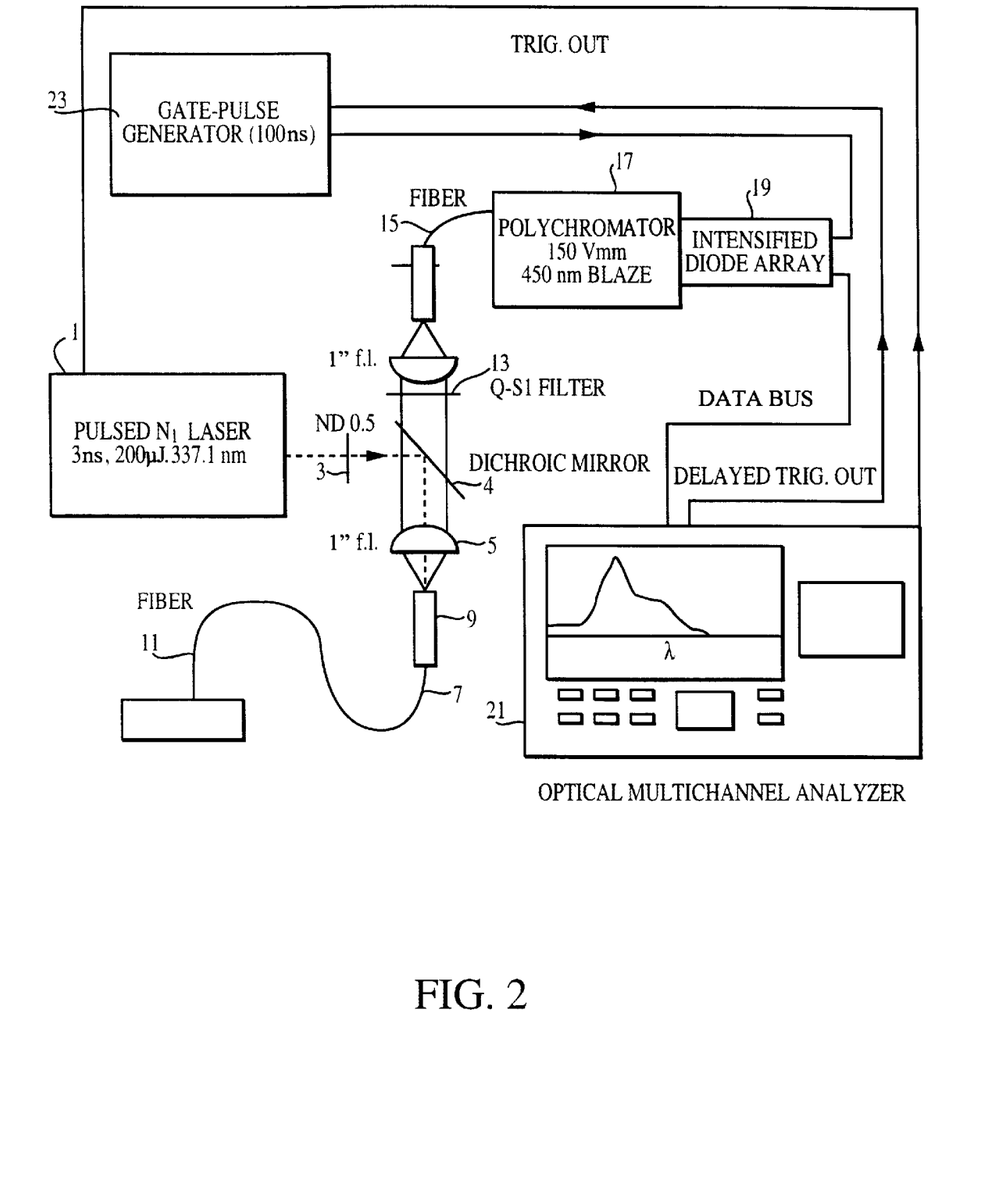
FIG. 2 is a schematic drawing showing a system for detecting laser-induced autofluoresence of inflamed and cancerous target tissue.

Autofluorescence can be detected using an optical fiber-based apparatus known in the art, e.g., as illustrated in FIG. 2. All the components of the apparatus are known in the art and are readily available. Output from a light source 1, e.g., a laser, passes through a filter 3, e.g., a neutral density filter, to a dichroic mirror 4. From there the light output is optically coupled via a quartz lens 5 to a single quartz optical fiber 7. The optical fiber 7 is passed through the working channel of a cystoscope 9 to irradiate a target tissue 11. Tissue autofluoresence is collected with the same optical fiber 7, and passed through a filter 13 and into a second fiber 15. This fiber is coupled to a polychromator (150 V, 450 nm blaze) 17, which is connected to an intensified diode array 19, and autofluoresence is recorded with an optical multichannel analyzer system 21. The analyzer system 21 is connected to a gate-pulse generator 23 and the light source 1.

Figure 3:
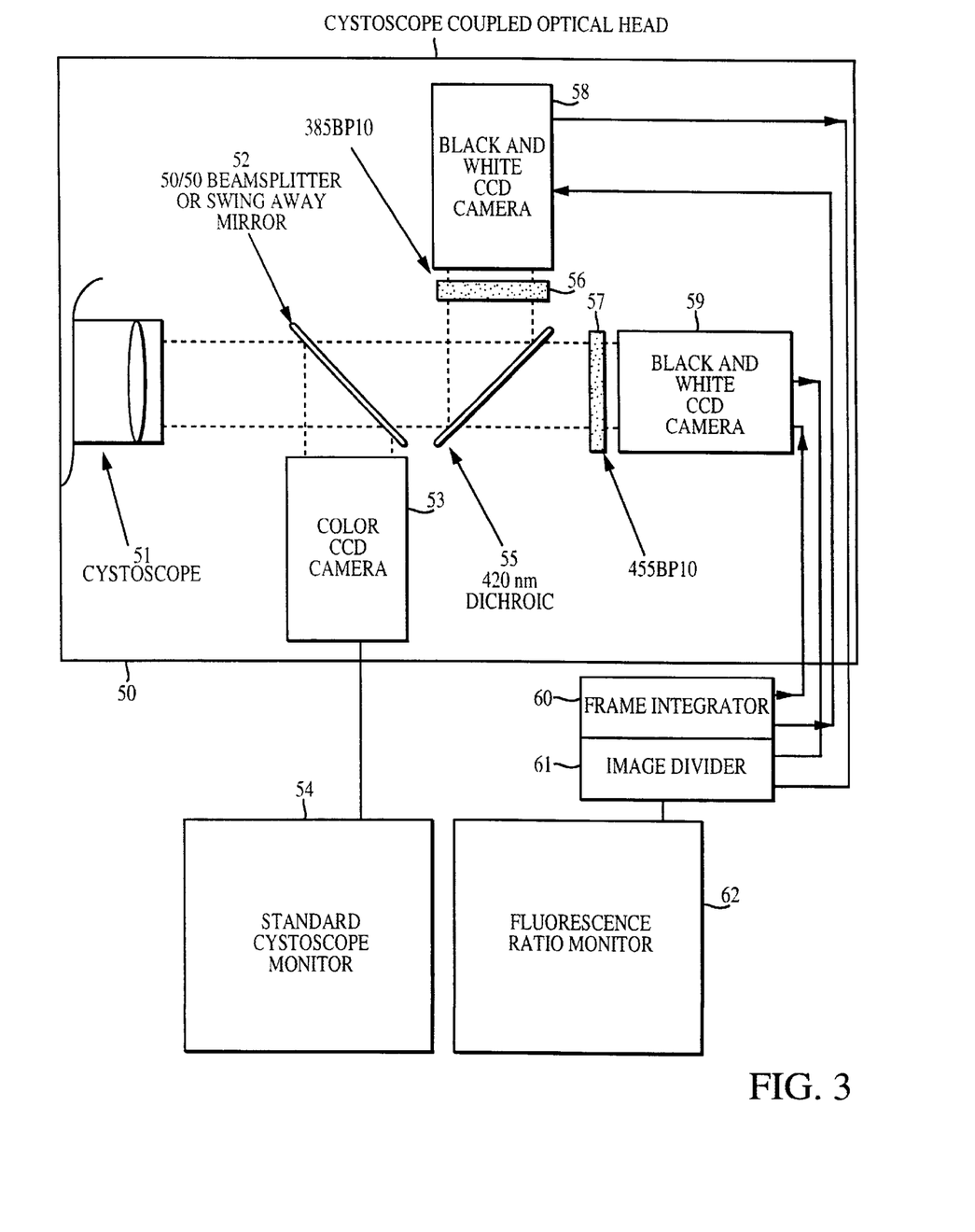
FIG. 3 is a schematic drawing showing an optical head for use with a cystoscope for detecting laser-induced autofluoresence of inflamed and cancerous target tissue.

In another embodiment, the cystoscope described above can be coupled to an optical head 50 as shown in FIG. 3. Tissue autofluoresence passes through a 50/50 beamsplitter 52, which also can be a swing-away mirror. The beamsplitter 52 can deflect the emitted autofluoresence to a color CCD camera 53, which is coupled to a standard cystoscope monitor 54. Alternatively, the beamsplitter 52 can transmit the emitted radiation to a dichroic mirror 55, which can reflect or transmit light (depending on the wavelength of the dichroic mirror) to first and second filters 56 and 57, e.g., the 385 BP10 and 455 BP10 filters shown in the figure. Here, the dichroic mirror 55 operates at 420 nm. Radiation transmitted through the filters 56 and 57 is transmitted into black and white CCD cameras 58 and 59, respectively. The CCD cameras 58 and 59 are connected to a frame integrator 60, which is in turn connected to a fluorescence ratio monitor 62, which can be any color CRT. The system can optionally include an image divider 61 connected between the black and white CCT cameras 58 and 59 and monitor 62.

Autofluoresence can be detected via a point measurement, e.g., by placing the tip of the fiber 11 against the tissue. Alternatively, autofluoresence can be detected over a wider area of target tissue by adding imaging optics to the tip of the fiber 11.

Methods of Detecting Autofluoresence

Using apparatuses such as those described above, the autofluorescence of a target tissue can be measured at desired wavelengths. In addition to detecting autofluoresence using endoscopes such as cystoscopes in non-surgical procedures, fluorescence can also be used on tissue that has been exposed, e.g., via surgical procedures.

Any incident radiation at a wavelength capable of inducing autofluoresence at wavelengths that distinguish inflamed and cancerous tissue can be used. Preferred wavelengths for the incident radiation are 325 to 350 nm, 330 nm to 343 nm, 335 nm to 340 nm, or 337 nm.

Emitted autofluoresence is measured at two predetermined wavelengths. Generally, these wavelengths are selected to correspond to those at which predominant chromophores of the irradiated tissues autofluoresce, and which can be used to distinguish cancerous from inflamed tissue. The first wavelength is selected to measure autofluoresence that decreases in cancerous tissue relative to inflamed tissue. Because decreased collagen autofluoresence is associated with tumorous tissues, the first wavelength can be one that results from collagen autofluoresence.

The second autofluoresence wavelength should be selected such that its intensity does not differ between cancerous and inflamed tissue. A ratio is then derived, e.g., by dividing the measured autofluoresence at the first wavelength, i.e., the wavelength at which autofluoresence is decreased in cancerous tissue relative to inflamed tissue, by the measured autofluoresence at the second wavelength, i.e., the wavelength at which autofluoresence is unchanged in cancerous and inflamed tissue.

To distinguish between cancerous and inflamed tissue, autofluoresence can be measured at a first wavelength of about 370–400 nm, 377–393 nm, 380–388 nm, or about 385 nm. The second wavelength can be about 440–470 nm, 447–463 nm, 450–460 nm, or about 455 nm. Other wavelengths centered around another peak for autofluorescence can also be used, as long as the intensity is essentially constant between cancerous and noncancerous tissue. In addition, the first and second wavelengths are chosen so that the autofluoresence of the chromaphore measured at the first wavelength does not contribute significantly to the autofluoresence signal measured at the second wavelength.

Care must be taken when administering the incident radiation. If, for example, a contact imaging system is used, e.g., optical fiber, excessive pressure of the probe may compress or pierce the apposed tissues, and autofluorescence could be detected from collagen-containing tissue in deeper layers. This could lead to an artificial false negative in the study.

Some noncancerous lesions show decreased collagen autofluoresence and can generate a low I385:I455 ratio. One such lesion is that caused by extensive cystitis glandularis, which is a form of nonneoplastic urothelial proliferation of the bladder. The increased number of cells in such lesions may mask the collagen signal.

The method can be used to distinguish cancerous lesions of the bladder such as CIS, TCC, including TaG1 (15), TaG2 and TaG3 from nonmalignant conditions associated with inflammation such as erythematous, edematous, and raised bladder lesions, acute cystitis, chronic cystitis, granulomatous cystitis, squamous metaplasia, mild dysplasia, and moderate dysplasia. The method can also distinguish inflamed lesions from cancerous lesions in other epithelial tissues, e.g., colon, esophagus, cervix, and lung tissue. Noncancerous, inflammatory disorders associated with these tissues include Crohn's disease and ulcerative colitis (colon), Barrett's esophagus, and inflammatory lesions in lungs associated with chronic tobacco smoking. When these epithelial tissues are examined, endoscopes appropriate for the particular tissue can be used to examine autofluoresence.

EXAMPLES

The invention will be further described in the following examples, which do not limit the scope of the invention described in the claims. The following examples illustrate the use of autofluoresence to distinguish inflamed and cancerous bladder tissue.

Example 1. Evaluation of I385:I455 Autofluoresence Ratios in

Normal, Inflamed. and Cancerous Bladder Tissue

Autofluoresence measurements were performed on 13 women and 40 men with bladder cancer undergoing mucosal biopsies or transurethral resection of the bladder at initial diagnosis, or at regular bladder tumor follow-up visits. Average patient age was 67 years (range 47 to 88).

Using a measuring apparatus as described in FIG. 2, tissue autofluoresence was excited by light pulses generated by a nitrogen laser. The output of the laser (337.1 nm, 3ns pulse at 10 Hz and 200 $\mu$J pulse energies) was coupled via a quartz lens into a 0.6 mm core diameter quartz optical fiber. Typical energies delivered to tissue were approximately 40 $\mu$J. The autofluoresence emitted from the tissue was transmitted via the same optical fiber and optically coupled to a 0.275 m polychromator. A fiber optic connector was used to couple the sterile fiber to the measuring system. The autofluoresence spectrum (300 to 800 nm) was recorded using an intensified 1,024 diode array optical multichannel analyzer system. The intensifier was gated with 100 ns pulses centered around the 3 ns laser pulses. Variations in laser energy and fiber coupling efficiencies were considered by measuring the autofluoresence from a cuvette of laser dye of known concentration on the day of the measurements. The multichannel analyzer recorded a complete spectrum with each laser pulse, and 50 spectra were collected and averaged for each measurement. Background spectra were measured daily and subtracted from all recorded tissue spectra. All spectra were also system response corrected by dividing the observed spectra by a system response curve, which was determined by measuring the spectral intensity of a calibrated 1,000 W quartz halogen lamp. The diode array was spectrally calibrated using a low pressure mercury lamp.

As the initial step, the bladder was visually inspected thoroughly to detect nodular, sessile or papillary tumors as well as suspicious (hypervascularized, edematous, raised and so forth) lesions of the urothelium. When biopsies or resections were needed for medical purposes, the quartz optical fiber was advanced through the working channel of a standard cystoscope and placed in gentle contact with the site of interest. The autofluoresence spectrum was then recorded within approximately 5 seconds using the optical multichannel analyzer system. Suspicious areas, visible papillary tumors, including adjacent normal appearing sites, and bladder areas in patients after previous treatment with chemotherapy combined with radiation therapy, as well as those treated with bacillus Calmette-Guerin, were included in this study to obtain basic information on different tissue types. All measured areas were biopsied immediately after the autofluoresence measurements using a flexible forceps advanced into position with the second working channel of the cystoscope to make sure the biopsy was obtained exactly from the measured point. At the end of the procedure, all suspicious areas and visible tumors were removed by standard transurethral resection. All tissue samples were fixed in formalin and submitted for routine pathological analysis. To decrease the potential for interobserver variability, autofluoresence measurements were performed by only two physicians using video camera guidance to ensure that the fiber was placed in gentle contact with the tissue surface.

The sensitivity, specificity, and positive and negative predictive values of laser-induced autofluorescence for detection of malignant versus nonmalignant urothelium were determined with standard statistical methods. A standard Student t test (two tailed, equal variance) and defined significance at $p<0.005$ were used to obtain the significance of autofluoresence differences between groups of different tissue types.

As determined by histological classification, there were 35 inflammatory (24 chronic and 11 acute), 42 normal, 1 squamous metaplastic, 7 dysplastic (3 stage D1 and 4 stage D2) and 28 malignant areas, as well as 1 carcinoma in situ included in the study. The 28 malignant lesions were stage Ta grades 1(15), 2(7), and 3(1), stage T1 grades 2(1) and 3(1), and stage T2 grade 3(3). Overall, 114 biopsies were obtained from 53 patients, for an average of 2.2 biopsies per patient (range 1 to 5).

After processing the autofluoresence spectra of the first 15 patients it was apparent that the autofluorescence of normal urothelium is up to 20 times greater than that of malignant lesions of the human bladder and is characterized by a strong peak of autofluoresence at about 385 nm (FIG. 1). There were also significant spectral differences between inflamed and cancerous tissue. While inflammatory areas and normal tissue always had two autofluoresence maxima at 385 and 455 nm, the typical spectra of malignant lesions showed only one maxima only at 455 nm. No further statistically significant spectroscopic differences could be found at 300 to 800 nm. Based on this data, the integrated autofluoresence intensity from 300 to 700 nm, and the ratio of autofluoresence intensities at 385 and 455 nm (I385:I455) were tested as two parameters by which to distinguish between the normal urothelium and the different bladder lesions.

Figure 4:
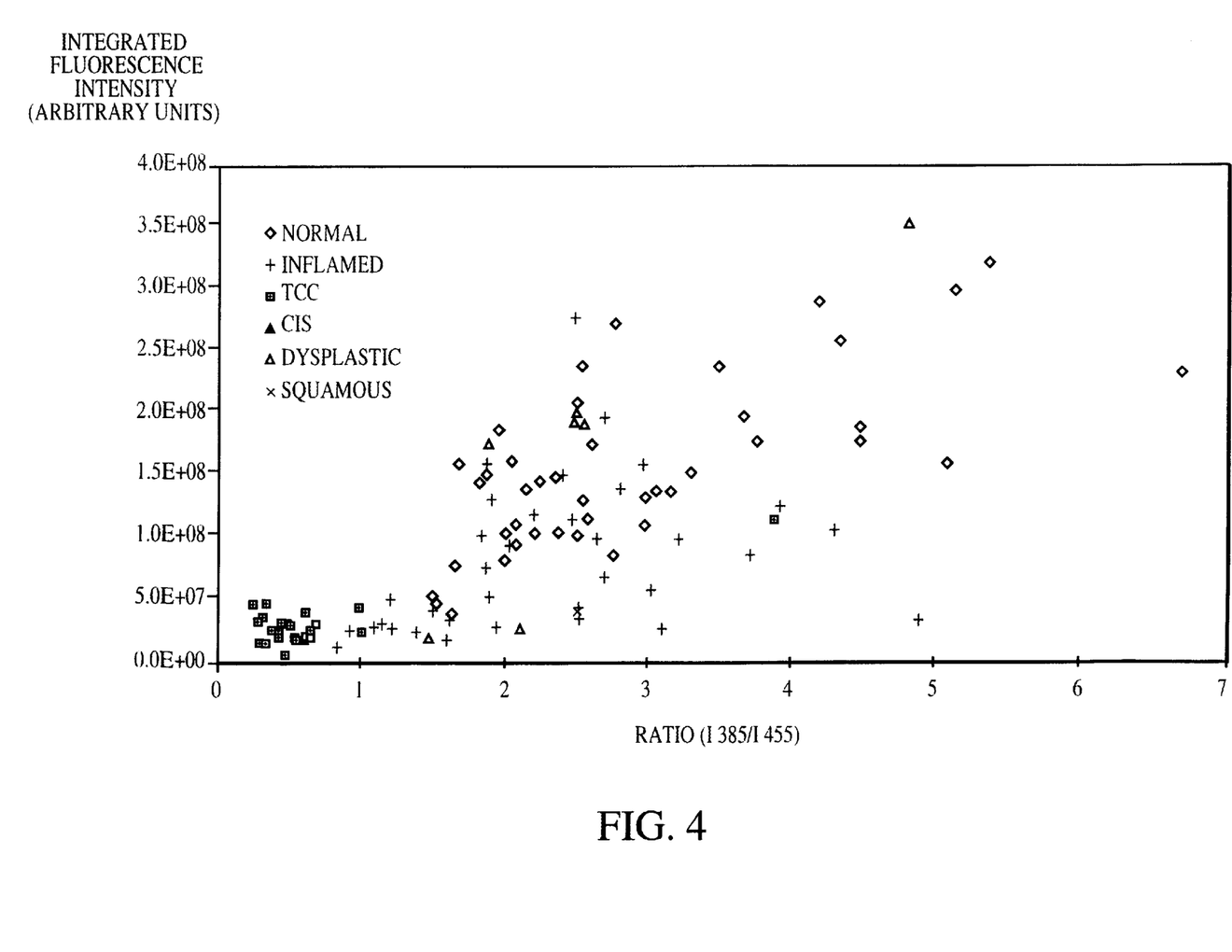
FIG. 4 is a graph showing the I385:I455 emission ratio plotted against integrated autofluoresence intensity of various bladder tissues.

The data for all 114 spectra analyzed in this manner are shown in FIG. 4 as a scatterplot of I385 and I455 autofluoresence parameters of the measured bladder areas. Integrated autofluoresence intensity (y axis) and ratio of autofluoresence intensities at 385 nm and 455 nm (x axis, I385:I455) are plotted for different histological states. TCC and Cis refer to transitional cell carcinoma and carcinoma in situ, respectively.

The data indicate that the I385:I455 ratio alone is sufficient to distinguish between inflamed and malignant tissue. Table I shows the I385:I455 ratio for different bladder tissues. The mean values of the ratio found for inflammation and normal urothelium were significantly different ($p<0.0001$) from those for malignant lesions. In addition, the mean value of the I385:I455 ratio seemed to decrease with progression of disease. I385:I455 ratios of less than 1.01 indicated cancerous tissue and ratios greater than 1.01 inflamed tissue.

TABLE I

| Bladder Areas (histological results) | I385:I455 Ratio | | | Total |
|---|---|---|---|---|
| | <1.01 | >1.01 | Mean ± SE | |
| All Patients | | | | |
| TCC | 27 | 1 | 0.63 ± 0.12[†] | 28 |
| Cis | 1 | 0 | 0.61 | 1 |
| Dysplasia | 0 | 7 | 2.53 ± 0.40 | 7 |
| Squamous metaplasia | 0 | 1 | 2.50 | 1 |
| Inflammation | 2 | 39 | 2.29 ± 0.16 | 36 |
| Normal urothelium | 0 | 42 | 2.89 ± 0.18 | 42 |
| Total No. Lesions | 30 | 84 | | 114 |
| Patients with Suspicious Bladder Lesions[#] | | | | |
| TCC | 9 | 1 | | 10 |
| Cis | 1 | 0 | | 1 |
| Dysplasia | 0 | 3 | | 3 |
| Inflammation | 2 | 22 | | 24 |
| Normal urothelium | 0 | 6 | | 6 |
| Total No. Lesions | 12 | 32 | | 44 |

[†]$p < 0.001$ compared to normal and inflamed urothelium.
[#]Suspicious lesions hypervascularized, edematous, and raised lesions.

There were 44 macroscopically suspicious (hypervascularized, edematous, raised and so forth) lesions in the study. On pathological analysis 11 lesions were malignant and 33 were nonmalignant. Except for 1 false-negative (micropapillary grade 1 tumor ) and 2 false-positive (extensive cystitis glandularis) results, all lesions could be classified correctly using the I385:I455 autofluoresence intensity ratio (see Table I). A total of 36 visually normal appearing sites (normal urothelium confirmed by pathology) adjacent to the visible primary tumor or to suspicious lesions of the bladder were measured and could be classified correctly as nonmalignant with the autofluoresence ratio (I385:I455). All 17 measured visible papillary tumors showed autofluoresence ratios <1.01. There were 17 measurements performed on nonmalignant urothelium altered by previous treatment with bacillus Calmette-Guerin or radiation with autofluoresence ration >1.01.

In the first 114 lesions evaluated, sensitivity, specificity, and positive and negative predictive values of the method for bladder cancer detection were 97, 98, 93, and 99%, respectively. However, differentiation of dysplastic bladder lesions (types D1 and D2) was not possible. Furthermore, no significant differences in autofluorescence could be detected between different stages (T1 to T3) or grades (1 to 3) of cancer.

The observed autofluoresence changes are likely due to optical effects of changes in the urothelium as well as to changes in the blood supply rather than to a change in metabolism of the tumor. During the measurements described above the bladder was filled with water, thinning the wall. The thickness of the urothelium in such a distended bladder is only 80 to 160 $\mu$m. Since 337 nm light is able to excite colonic tissue layers as deep as 500 $\mu$m, it is expected that autofluoresence from the lamina propria and muscle layers of the bladder wall is also excited by a nitrogen laser. NADPH and NADH are primarily located on the metabolically active layer of muscle cells, but they are also found in the other bladder layers. In contrast to the lamina propria and muscle, there is no collagen in the urothelium. Since collagen is predominantly in the lamina propria, the increased thickness of the urothelium could lead to the observed loss of the 385 nm peak in malignant lesions by filtering of the autofluorescence from deeper layers. The increased blood supply of small malignant lesions could cause an additional decrease in autofluoresence due to broad absorption bands of (oxy)hemoglobin between 300 and 600 nm.

Example 2. Further Evaluation of I385:I455 Autofluoresence

Ratios on Suspicious Bladder Areas

Figure 5:
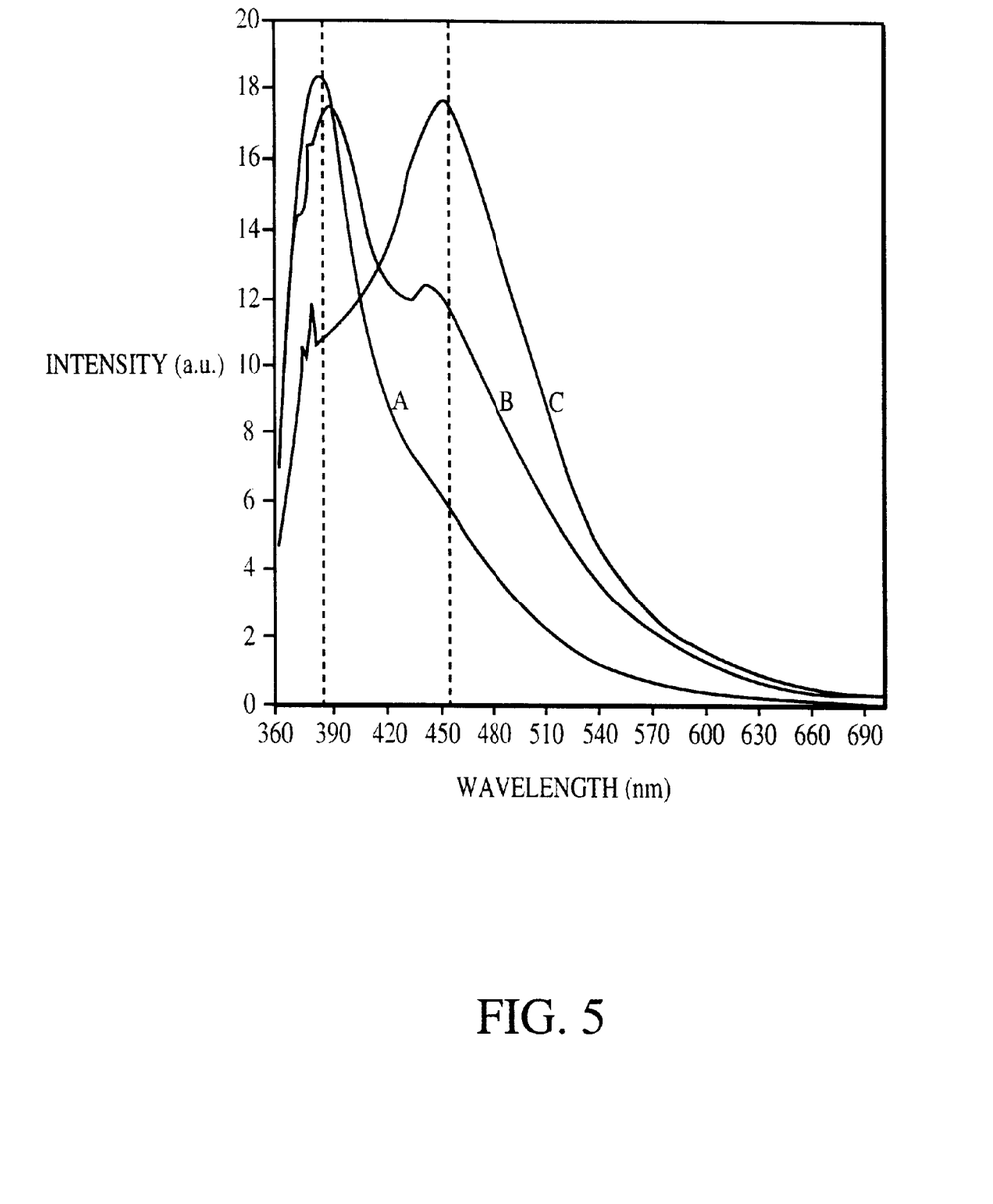
FIG. 5 is a series of mean autofluoresence spectra of normal urothelium (A), carcinoma in situ (B), and transitional cell carcinoma (TCC).

To further evaluate the feasibility of measuring I385:I455 ratios as a way to differentiate inflamed and malignant bladder tissue, an additional 86 suspicious bladder areas, i.e., either inflamed or malignant, areas were examined using the methods describe in Example 1 in 75 additional patients (17 female, 58 male) with an average age of 68 (range 47 to 88). Table II includes the 44 bladder lesions termed suspicious in Table I as well as the additional 86 bladder areas. As determined by histological classification, 23 (18%) biopsies were taken from malignant and 107 biopsies (82%) were taken from nonmalignant bladder areas. FIG. 5 shows the averaged autofluoresence spectra for all normal areas (A), Cis (B), and TCC (C). While the spectrum of normal urothelium showed a maximum of 385 nm, the spectrum of TCC was characterized by a maximum at 455 nm. Both autofluoresence maxima were found for Cis, but the first maximum was shifted to 392 nm and the second maximum was shifted to 444 nm. After calculating and analyzing the ratio (I385:I455), significant differences could be found between malignant and nonmalignant areas of the bladder ($p<0.001$).

TABLE II

| BLADDER AREAS (HISTOLOGY) | $(I_{385}:I_{455})$* | NUMBER (total) |
|---|---|---|
| Nonmalignant | 2.44 ± 1.14 | 107 |
| Normal | 2.88 ± 1.29 | 40 |
| Acute Cystitis | 2.50 ± 0.62 | 3 |
| Chronic Cystitis | 2.31 ± 0.96 | 38 |
| Granulomatous Cystitis | 2.24 ± 1.08 | 3 |
| Cystitis Glandularis | 0.93 | 1 |
| Giant Cell Cystitis | 0.64 ± 0.28 | 2 |

TABLE II-continued

| BLADDER AREAS (HISTOLOGY) | $(I_{385}:I_{455})$* | NUMBER (total) |
|---|---|---|
| Squamous Metaplasia | 2.52 | 1 |
| Hyperplasia | 1.53 ± 0.41 | 3 |
| Mild Dysplasia | 2.93 ± 0.94 | 6 |
| Moderate Dysplasia | 1.67 ± 0.57 | 10 |
| Malignant | 0.89 ± 0.75 | 23 |
| Cacinoma in situ | 1.08 ± 0.48 | 6 |
| TCC (TaG1) | 0.83 ± 1.08 | 10 |
| TCC (TaG2) | 0.54 ± 0.23 | 2 |
| TCC (T1G2) | 1.01 | 1 |
| TCC (T2G3) | 0.88 ± 0.17 | 4 |
| TOTAL | | 130 |

*mean values and standard deviation

Within the subgroup of nonmalignant areas, autofluoresence ratios (I385:455) of "proliferative" and/or sometimes tumor-like lesions (squamous metaplasia, dysplasia, hyperplasia, cystitis glandularis, granulomatous cystitis, giant cell cystitis) were significantly different from those of normal and acute/chronic inflamed tissue (p<0.01).

Figure 6:
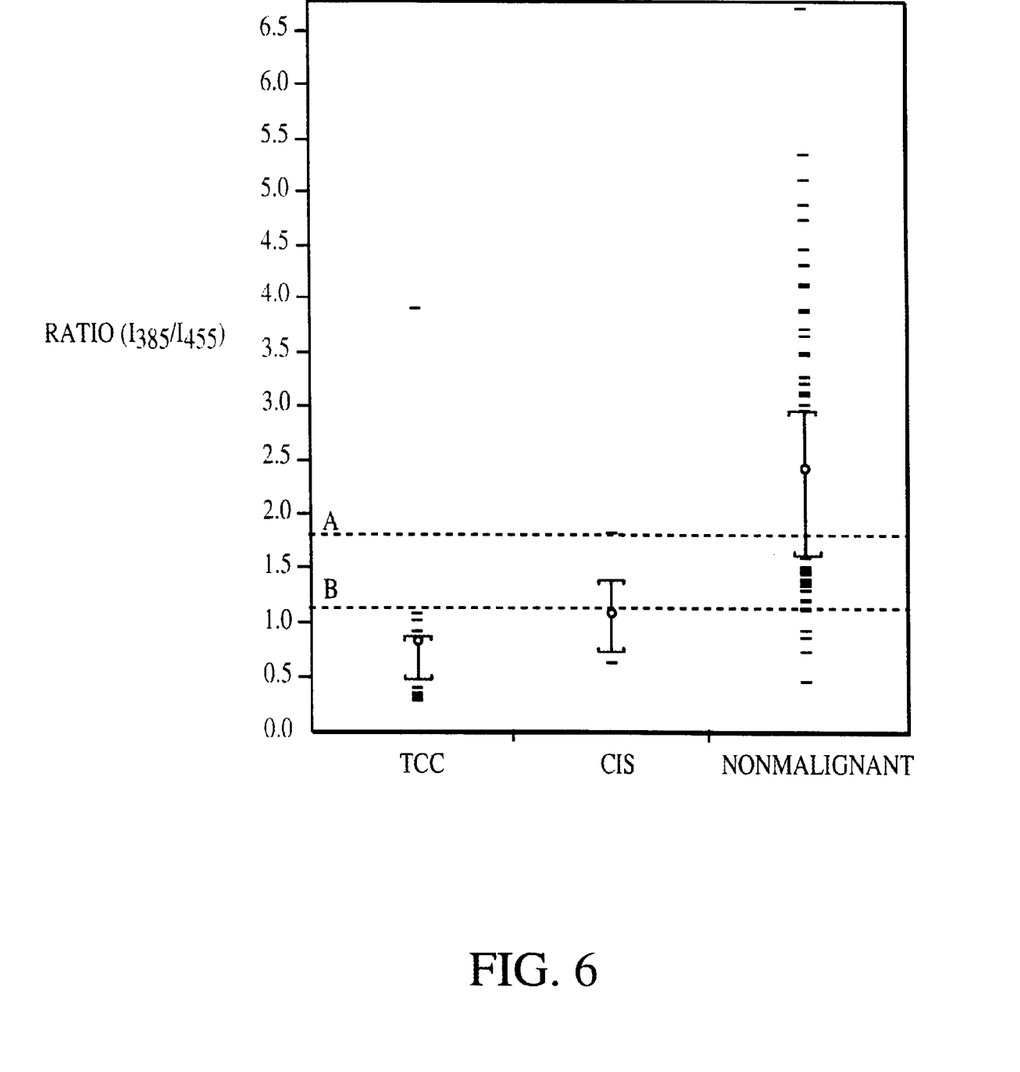
FIG. 6 is a histogram showing the autofluoresence ratios for groups of transitional cell carcinoma (TCC), carcinoma in situ (Cis), and nonmalignant tissues.

FIG. 6 shows the autofluoresence ratios of all measured bladder areas grouped into TCC, Cis, and nonmalignant, i.e., inflamed, areas. The mean values (center of error bar), 75th percentile (upper limit of error bar), and 25th percentile (lower limit of error bar) are shown. 95% of the calculated ratios for malignant tissues fell below dotted line A (which intercepts the y-axis at an I385:I455 ratio of 1.78), while 5% of the ratios calculated for nonmalignant tissues fell below dotted line B (which intercepts the y-axis at a I385:455 ratio of about 1.1).

The difference between TCC and Cis was not statistically significant (p=0.47). However, there was a significant difference between Cis and TCC compared to nonmalignant tissue (p<0.0005) as well as between Cis and TCC compared to acute/chronic inflamed lesions (p<0.003). There was also a significant difference between the I385:I455 ratios of Cis and "proliferative" nonmalignant lesions (p<0.05). Statistical analysis showed that 95% of all nonmalignant areas had a ratio (I385:I455) above 1.1 and 95% of all malignant lesions had a ratio below 1.78. By taking the latter value as the detection criterion to separate malignant from nonmalignant areas, only 30 nonmalignant areas would have been classified as "malignant." Taking into account the 107 nonmalignant areas, which were biopsied during routine white light cystoscopy, the use of the LIF ratio (I385:I455) would reduce the number of biopsies taken from nonmalignant tissue by 77 (72%).

Figure 7:
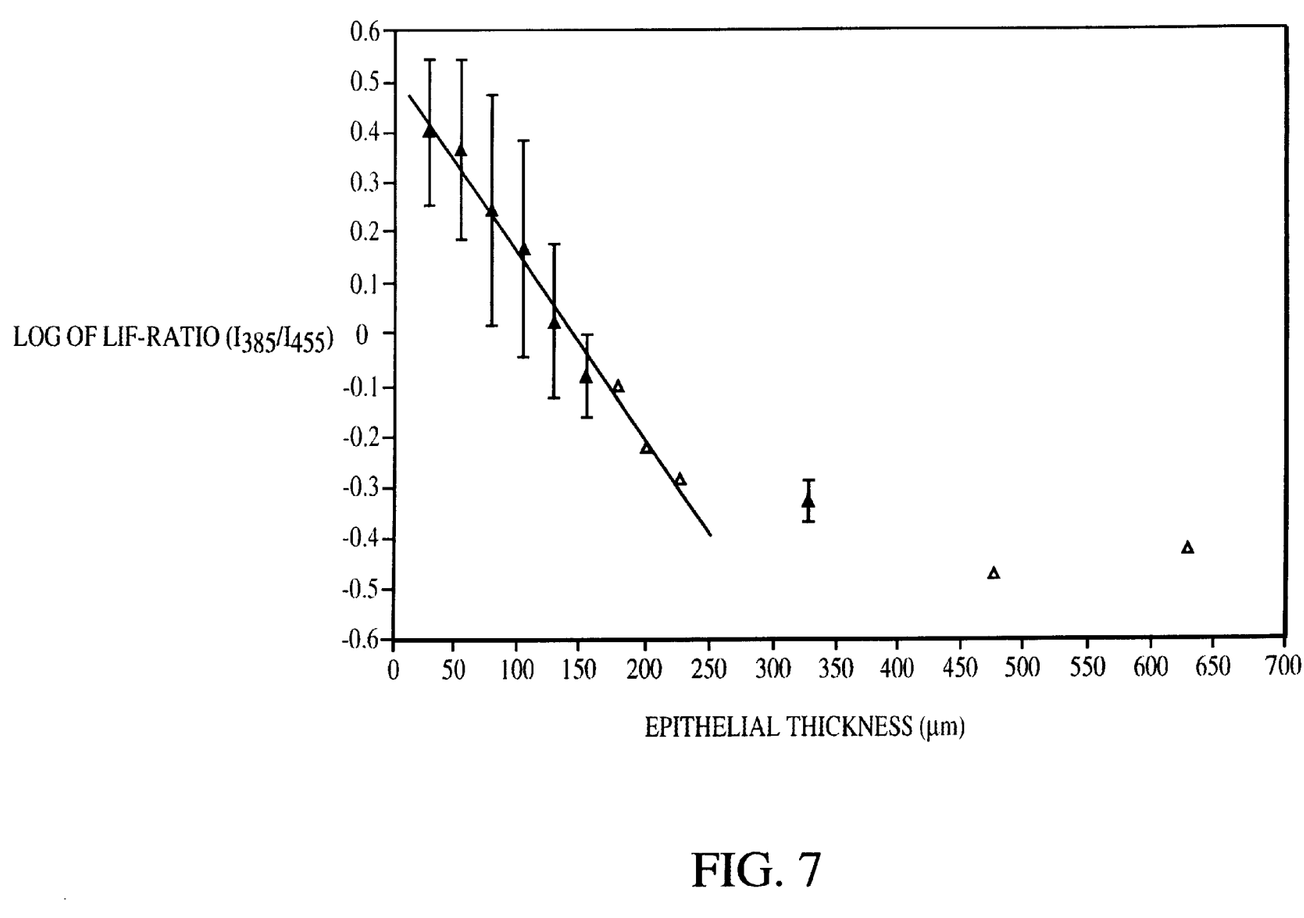
FIG. 7 is a graph showing the correlation between the I385:I455 autofluoresence ration and the thickness of the displayed epithelium for all bladder areas.

The autofluoresence data were analyzed for the best fit to a dependence of the ratio (I385:I455) on epithelial thickness (tested dependencies: linear, logarithmic, exponential, polynomial, power, moving average). The best fit was exponential; the autofluoresence ratio was found to decrease exponentially with increasing epithelial thickness in the range between 1 and 225 $\mu$m. In FIG. 7 the logarithm of the autofluoresence ratio versus epithelial thickness is plotted; the Pearson product-moment correlation coefficient of the resultant linear function r is −0.71. The magnitude of the coefficient suggests a negative exponential association between epithelial thickness ($\leq 225$ $\mu$m) and the ratio (I385:I455).

The purpose of this study was to apply the diagnostic algorithm I385:I455 to a larger series of 130 suspicious bladder areas and random biopsy sites. The averaged autofluoresence spectra of malignant and normal bladder areas, which are the basis for the diagnostic algorithm, were similar to those in Example 1 with maxima at 385 nm and 455 nm for normal tissue, respectively.

The hypothesis that the autofluoresence spectrum is influenced by the thickness of the bladder epithelium is supported by the fact that lower I385:455 ratios were found for proliferative lesions within the group of nonmalignant areas. Furthermore, by plotting the I385:I455 ratio of all measured bladder areas versus epithelial thickness, an exponential decay was found for the LIF ratio with increasing epithelial thickness up to 225 $\mu$m (FIG. 7). Beyond 225 $\mu$m, no further decay of the I385:455 ratio was observed, which suggests that most of the measured autofluorescence originates from the uppermost 225 $\mu$m.

The large scatter in the I385:I455 ratios of different bladder lesions can be attributed to various factors. Despite the effort that was made to take biopsies exactly from the measured bladder areas, and due to the fact that the measuring fiber has a small sampling volume, it is possible that the histological sample is not taken exactly from the measured site. Furthermore, the filling of the bladder during the autofluoresence measurement as well as the condition of the tissue sample by the time it was fixed in formalin can lead to discrepancies between the epithelial thickness in vivo and on the histology slide. Finally, different degrees of blood absorption could also explain part of the scatter in the ratios of different bladder lesions and may confirm the hypothesis that epithelial thickness and blood concentrations are the main determinants for the autofluoresence signal measured from the bladder surface.

Since it is unlikely that there are major thickness differences between normal tissue and acute chronic inflamed tissue, changes in the autofluoresence ratio are most likely due to increased blood absorption. In the present study, the ratio decreased from a mean value of 2.88 for normal tissue to a mean value of 2.31 for chronic cystitis (Table 2). The lowest ratio found for nonmalignant lesions was 1.08. Visually, some of the inflammatory lesions have a similar appearance (erythromatous, flat) to malignant lesions, indicating a similar amount of superficial blood. Reflectance measurements also show no evidence for differences in blood concentration between these inflammatory lesions and malignant areas. Thus, it seems that only the additional increase of epithelial thickness in malignant lesions leads to the observed further decrease of the autofluoresence ratio to a mean value of 0.89 for malignant lesions. The lowest ratio found for malignant lesions was 0.28.

In Example 1, a ratio of 1.01 was chosen as the parameter to distinguish between inflamed and cancerous bladder areas. In the present study 95% of nonmalignant areas showed a autofluoresence ratio of above 1.01, which is only slightly smaller than the results of the first study where 98% of these areas were above a ratio of 1.01. In the present study 22% of the malignant lesions had a autofluoresence ratio above 1.01 compared to only 3% in the first data set. The difference can be explained by a larger number of Cis tumors, and the exclusion of obvious papillary tumors in the present study. 50% of Cis have a autofluoresence ratio above 1.01 compared to only 11% of TCC.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for distinguishing cancerous tissue from inflamed tissue in a patient, the method comprising:
   (a) exposing a target tissue suspected of containing inflamed or cancerous tissue to incident radiation having a wavelength between 325 and 350 nm;
   (b) detecting autofluorescence emitted at a first wavelength between 370 and 400 nm and at a second wavelength between 440 and 470 nm after irradiation of the target tissue with the incident radiation; and
   (c) comparing the intensity of the autofluorescence emitted at the first wavelength with the intensity of the autofluorescence emitted at the second wavelength, wherein a decrease in autofluorescence intensity at the first wavelength compared to autofluorescence intensity emitted at the second wavelength indicates cancerous cells within the target tissue.

2. The method of claim 1, wherein the incident radiation has a wavelength between 335 and 340 nm.

3. The method of claim 1, wherein the incident radiation has a wavelength of 337 nm.

4. The method of claim 1, wherein the first wavelength is between 377 and 393 nm.

5. The method of claim 1, wherein the first wavelength is centered at about 385 nm.

6. The method of claim 1, wherein the second wavelength corresponds to reduced nicotine adenine dinucleotide phosphate (NADPH) or reduced nicotine adenine dinucleotide (NADH).

7. The method of claim 1, wherein the second wavelength is between 450 and 460 nm.

8. The method of claim 1, wherein the second wavelength it centered at about 455 nm.

9. The method of claim 1, wherein the second wavelength is 455 nm.

10. The method of claim 1, wherein the patient is a human.

11. The method of claim 1, wherein the tissue is bladder tissue.

12. The method of claim 1, wherein the method is performed without a sensitizing agent.

13. An apparatus for distinguishing cancerous and inflamed tissue, the apparatus comprising:
   (a) a light source having a wavelength between 325 and 350 nm;
   (b) a first detector to detect autofluoresence emitted from the irradiated target tissue at a first wavelength between 370 and 400 mn;
   (c) a second detector to detect autofluoresence emitted from the irradiated target tissue at a second wavelength between 440 and 470 nm;
   (d) an analyzer that compares a threshold value to the ratio of the intensity of the autofluoresence at the first wavelength and the intensity of the autofluoresence at the second wavelength, wherein a ratio below the threshold value indicates that the analyzed tissue is cancerous, and a ratio above the threshold indicates that the analyzed tissue is inflamed or normal.

14. A method for distinguishing cancerous tissue from inflamed tissue in a patient, the method comprising:
   (a) exposing a target tissue suspected of containing inflamed or cancerous tissue to incident radiation having a wavelength between 325 and 350 nm;
   (b) detecting autofluoresence emitted at a first wavelength between 370 and 400 nm and at a second wavelength between 440 and 470 nm upon irradiation of the target tissue with the incident radiation; and
   (c) comparing a threshold value to a ratio of the intensity of autofluoresence at the first wavelength to the intensity of autofluoresence at the second wavelength, wherein a ratio below the threshold value indicates that the analyzed tissue is cancerous, and a ratio above the threshold indicates that the analyzed tissue is inflamed or normal.

15. The method of claim 14, wherein the threshold value is 0.9.

16. The method of claim 14, wherein the threshold value is 1.01.

17. The method of claim 14, wherein the threshold value is 1.78.

* * * * *